US 8,396,267 B2

(12) United States Patent
Lake et al.

(10) Patent No.: US 8,396,267 B2
(45) Date of Patent: Mar. 12, 2013

(54) CORRECTING SUBJECT MOTION IN MULTIPLE RESOLUTIONS IN MAGNETIC RESONANCE IMAGING

(75) Inventors: David S. Lake, Rochester, MN (US); Armando Manduca, Rochester, MN (US); Jeffrey S. McAllister, St. Paul, MN (US); Timothy J. Mullins, Blaine, MN (US); Nelson Ramirez, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 668 days.

(21) Appl. No.: 12/612,105

(22) Filed: Nov. 4, 2009

(65) Prior Publication Data
US 2011/0105882 A1      May 5, 2011

(51) Int. Cl.
*G06K 9/00* (2006.01)
(52) U.S. Cl. ...................................... 382/128
(58) Field of Classification Search .................. 382/128, 382/131, 295; 600/410, 415
See application file for complete search history.

(56) References Cited

U.S. PATENT DOCUMENTS

| | | | | |
|---|---|---|---|---|
| 6,144,873 A * | 11/2000 | Madore et al. | ............... | 600/410 |
| 6,647,134 B1 * | 11/2003 | McGee et al. | ............... | 382/128 |
| 7,308,125 B2 * | 12/2007 | Atkinson | ................. | 382/131 |
| 7,561,909 B1 * | 7/2009 | Pai et al. | ................. | 600/410 |
| 7,786,728 B2 * | 8/2010 | Fukuta | ..................... | 324/307 |
| 8,265,353 B2 * | 9/2012 | Bonnet et al. | .............. | 382/128 |
| 2006/0226836 A1 * | 10/2006 | Shu et al. | ............... | 324/309 |
| 2008/0054899 A1 * | 3/2008 | Aksoy et al. | ............... | 324/307 |
| 2008/0129290 A1 * | 6/2008 | Yao | ............... | 324/309 |
| 2008/0169808 A1 * | 7/2008 | Taniguchi et al. | ........... | 324/307 |
| 2008/0287772 A1 * | 11/2008 | Declerck et al. | ............ | 600/411 |
| 2009/0010514 A1 * | 1/2009 | Kimura | ................. | 382/131 |
| 2009/0115794 A1 * | 5/2009 | Fukuta | ..................... | 345/581 |

OTHER PUBLICATIONS

Wang et al ("Retrospective adaptive motion correction for navigator-gated 3D coronary MR angigraphy", Journal of Magnetic Resonance Imaging, vol. 11, Issue 2, p. 208-214, Feb. 2000).*

\* cited by examiner

*Primary Examiner* — Claire X Wang
*Assistant Examiner* — Shervin Nakhjavan
(74) *Attorney, Agent, or Firm* — Patterson & Sheridan, LLP

(57) ABSTRACT

Systems, methods and articles of manufacture are disclosed for compensating for motion of a subject during an MRI scan of the subject. k-space data may be received from the MRI scan of the subject. A first graphical image may be generated from a first set of data elements from the k-space data. Similarly, a second graphical image may be generated from a second set of data elements from the k-space data. An offset in pixels may be determined by which to translate the second graphical image from the first graphical image to compensate for the motion. The k-space data may be modified at a sub-pixel offset relative to the determined offset. A motion-compensated graphical image of the subject may be generated from the modified k-space data. Doing so reduces the search space evaluated to sharpen images generated from the k-space data.

21 Claims, 11 Drawing Sheets

WITH MOTION

IMAGE SPACE (LOWER RESOLUTION SEARCH)

KSPACE (HIGHER RESOLUTION SEARCH)

CORRECTING SUBJECT MOTION IN MULTIPLE RESOLUTIONS IN MAGNETIC RESONANCE IMAGING

STATEMENT REGARDING FEDERALLY SPONSORED RESEARCH OR DEVELOPMENT

This invention was made with government support under EB000229 awarded by the National Institute of Biomedical Imaging and Bioengineering. The government has certain rights in the invention.

BACKGROUND OF THE INVENTION

1. Field of the Invention

Embodiments of the invention relate to motion correction. More specifically, embodiments of the invention relate to motion correction in a magnetic resonance imaging (MRI) environment.

2. Description of the Related Art

Motion correction refers to a post-processing technique for compensating for patient motion during a magnetic resonance imaging (MRI) scan. Motion correction may be used to generate graphical images that more accurately depict a patient during the MRI scan, notwithstanding movement by the patient during the MRI scan. One such technique involves superimposing sub-images at different offsets from each other to reduce blur. Each sub-image corresponds to a different point in time during the MRI scan and is generated from frequency domain data acquired during the MRI scan. For example, a second partial image may be taken one millisecond after a first partial image. Another such technique involves directly modifying frequency domain data acquired during the MRI scan. For example, a graphical image may be generated from each proposed modification to the frequency domain data. The graphical images may be evaluated to select a modification that yields the sharpest graphical image.

SUMMARY OF THE INVENTION

One embodiment of the invention includes a method for compensating for motion of a subject during a magnetic resonance imaging (MRI) scan of the subject. The method may generally include receiving k-space data from the MRI scan of the subject. The k-space data itself may include frequency domain data acquired from the MRI scan used to generate a graphical image of the subject. Also, the frequency domain representation includes a plurality of data elements, including a first set of data elements acquired at a first point in time during the MRI scan and a second set of data elements acquired at a second point in time during the MRI scan. The method may also include generating a first graphical image from the first set of data elements, generating a second graphical image from the second set of data elements, and determining an offset in pixels by which to translate the second graphical image from the first graphical image to compensate for the motion. The method may also include modifying the k-space data based on the determined offset to compensate for the motion to a sub-pixel offset, relative to the determined offset, and generating a motion-compensated graphical image of the subject from the modified k-space data.

Another embodiment includes a computer readable storage medium containing a program which, when executed, performs an operation for compensating for motion of a subject during a magnetic resonance imaging (MRI) scan of the subject. The operation may generally include receiving k-space data from the MRI scan of the subject. The k-space data itself may include frequency domain data acquired from the MRI scan used to generate a graphical image of the subject. Also, the frequency domain representation includes a plurality of data elements, including a first set of data elements acquired at a first point in time during the MRI scan and a second set of data elements acquired at a second point in time during the MRI scan. The operation may also include generating a first graphical image from the first set of data elements, generating a second graphical image from the second set of data elements, and determining an offset in pixels by which to translate the second graphical image from the first graphical image to compensate for the motion. The operation may also include modifying the k-space data based on the determined offset to compensate for the motion to a sub-pixel offset, relative to the determined offset, and generating a motion-compensated graphical image of the subject from the modified k-space data.

Still another embodiment includes a system having one or more computer processors and a memory. The memory may store a program executed by the one or more computer processors. The program may generally be configured to perform an operation for compensating for motion of a subject during a magnetic resonance imaging (MRI) scan of the subject.

The operation may generally include receiving k-space data from the MRI scan of the subject. The k-space data itself may include frequency domain data acquired from the MRI scan used to generate a graphical image of the subject. Also, the frequency domain representation includes a plurality of data elements, including a first set of data elements acquired at a first point in time during the MRI scan and a second set of data elements acquired at a second point in time during the MRI scan. The operation may also include generating a first graphical image from the first set of data elements, generating a second graphical image from the second set of data elements, and determining an offset in pixels by which to translate the second graphical image from the first graphical image to compensate for the motion. The operation may also include modifying the k-space data based on the determined offset to compensate for the motion to a sub-pixel offset, relative to the determined offset, and generating a motion-compensated graphical image of the subject from the modified k-space data.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
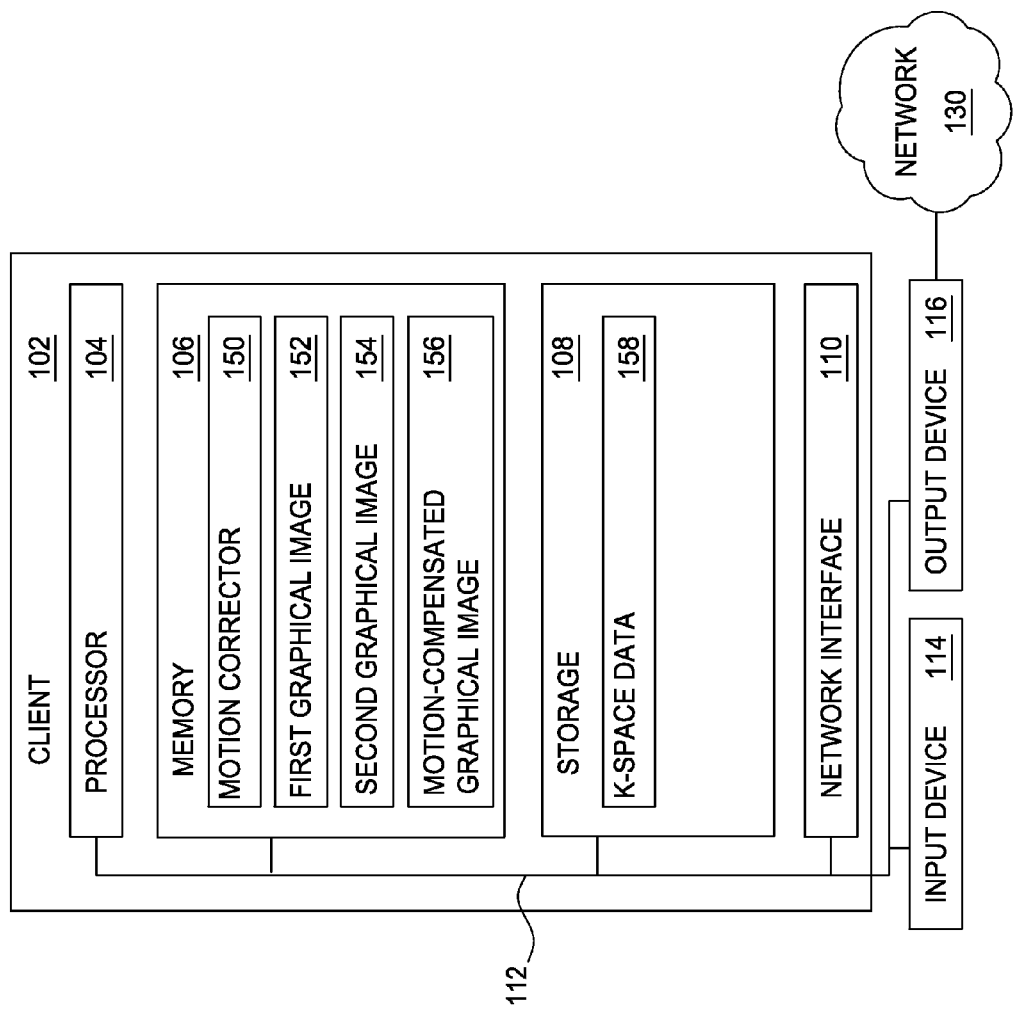
FIG. 1 is a block diagram illustrating a system for compensating for motion of a subject during an MRI scan of the subject, according to one embodiment of the invention.

Embodiments of the present invention generally compensate for motion by a subject during an MRI scan of the subject. A subject refers to any living organism or animal to which imaging technology may be applied. One embodiment of the invention provides a motion corrector. The motion corrector may generate graphical images that more accurately depict a subject (e.g., a patient) during the MRI scan, notwithstanding movement by the subject during the MRI scan. In one embodiment, the motion corrector may compensate for a translational motion of the subject between a first point in time during the MRI scan and a second point in time during the MRI scan. A search space for motion correction between the first point in time and the second point in time may be a set of all possible patient motions occurring between the first point in time and the second point in time.

In the following, k-space refers to a temporary image space (not to be confused with an image space corresponding to a graphical image) in which data from digitized magnetic resonance (MR) signals (e.g., frequency domain data) may be stored during data acquisition (i.e., during an MRI scan). When k-space is full (i.e., when the MRI scan is complete), the k-space data may be processed (e.g., via a discrete Fourier transform (DFT), such as a 2D fast Fourier transform (FFT)) to produce a final image. Thus, k-space holds raw data from an MRI scan prior to image construction. For example, the k-space data may be a grid of complex numbers that store the frequency domain data acquired from the MRI scan.

In one embodiment, a subject motion may be described in terms of pixels of a graphical image (i.e., of the subject). For example, between a first point in time and a second point in time (e.g., 1 millisecond after the first point in time) during an MRI scan, an arm of a patient may move to the right by 4.25 pixels. Such movement by the patient during the MRI scan may yield a blurry graphical image of the arm. Suppose a first row of the k-space data is acquired by the MRI scan at the first point in time and a second row of the k-space data is acquired at the second point in time. Specifically, any image blurriness may be due to the first and second rows of the k-space data representing different spatial locations of the arm of the subject (namely, at the relative locations of (0,0) pixels and (+4.25, 0) pixels). To compensate for such a movement, for example, the motion corrector may modify the second row of data to (in effect) correct the movement by 4.25 pixels. However, the motion corrector may not have any basis to determine what specific correction to make (e.g., 4.25 pixels to the left). For example, patient motion during the MRI scan may not have been captured. Even if motion information is captured, the motion information may not always be available to the motion corrector.

While the motion corrector may attempt to search all possible subject motions occurring between the first point in time and the second point in time, such a search may be so computationally expensive as to be unfeasible, even if not all possible subject motions are evaluated. Further, failing to search all possible subject motions may yield a sub-optimal result.

In one embodiment, the motion corrector may generate graphical images corresponding to data acquired at different points in time during the MRI scan. A graphical image generated from data acquired at a single point in time during the MRI scan may also be referred to herein as a "sub-image." The motion corrector may determine an offset (measured in discrete pixels) by which to superimpose the sub-images over each other to yield a sharper graphical image. The motion corrector may determine a sub-pixel offset (relative to the determined offset) by which to superimpose the sub-images over each other to yield an even sharper graphical image. However, because the sub-images may not support translations to sub-pixel offsets, the motion corrector may (in effect) perform a sub-pixel translation by: (i) directly modifying the k-space data (e.g., only rows of the k-space data from which the sub-image to be translated is to be generated) and (ii) generating a new sub-image from the modified k-space data.

In one embodiment, the motion corrector may generate a graphical image that corrects for motion to a finer resolution than discrete pixels of the graphical image. Further, the motion corrector may generate a motion-compensated graphical image more efficiently than searching a space of possible patient motions that may have occurred between the first point in time and the second point in time (i.e., because the search space is reduced). In other words, the motion corrector may search for sub-pixel offsets (and thereby search for precise patient motions) more efficiently because the motion corrector only searches sub-pixel offsets (in k-space) relative to a determined offset (in discrete pixels). For example, the motion corrector may modify the second row of the k-space data based on a discrete pixel offset of 4 pixels to the right and a sub-pixel offset of 0.25 pixels to the right (for a total of 4.25 pixels to the right). Further still, the motion corrector may generate a motion-compensated graphical image that more accurately depicts a subject during an MRI scan, notwithstanding movement by the subject during the MRI scan. In effect, the motion corrector may reduce the search space to generate graphical images from the k-space data more efficiently and more accurately.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

FIG. 1 is a block diagram illustrating a system 100 for compensating for subject motion that occurs during an MRI scan, according to one embodiment of the invention. The networked system 100 includes a computer 102. The computer 102 generally includes a processor 104 connected via a bus 112 to a memory 106, a network interface device 110, a storage 108, an input device 114, and an output device 116. The computer 102 is generally under the control of an operating system (not shown). Examples of operating systems include UNIX, versions of the Microsoft Windows® operating system, and distributions of the Linux® operating system. (Note: Linux is at trademark of Linus Torvalds in the United States and other countries.) More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single entity, it should be understood that the memory 106 may comprise a plurality of modules, and that the memory 106 may exist at multiple levels, from high speed registers and caches to lower speed but larger DRAM chips. The network interface device 110 may be any type of network communications device allowing the computer 102 to communicate with other computers via the network 130. In general, the network 130 may be a telecommunications network and/or a wide area network (WAN). In a particular embodiment, the network 130 is the Internet.

The input device 114 may be any device for providing input to the computer 102. For example, a keyboard, keypad, light pen, touch-screen, track-ball, or speech recognition unit, audio/video player, and the like may be used. The output device 116 may be any device for providing output to a user of the computer 102. For example, the output device 116 may be any conventional display screen or set of speakers, along with their respective interface cards, i.e., video cards and sound cards (not shown). Although shown separately from the input device 114, the output device 116 and input device 114 may be combined. For example, a display screen with an integrated touch-screen, a display with an integrated keyboard, or a speech recognition unit combined with a text speech converter may be used.

The storage 108 may be a hard disk drive storage device. Although the storage 108 is shown as a single unit, the storage 108 may be a combination of fixed and/or removable storage devices, such as fixed disc drives, floppy disc drives, tape drives, removable memory cards, or optical storage. The memory 106 and the storage 108 may be part of one virtual address space spanning multiple primary and secondary storage devices.

As shown, the memory 106 of the computer 102 includes a motion corrector 150, a first graphical image 152, a second graphical image 154, and a motion-corrected graphical image 156. The motion corrector 150 may provide a software application executed by the processor 104 to transform raw image data, e.g., to reduce the blurriness (or stated conversely to sharpen the clarity) of an image generated from k-space data by effecting transformations to k-space data as described in greater detail below. Further, the storage 108 of the computer 102 includes k-space data 158. FIGS. 2 through 10 and associated descriptions detail the structure and operation of the motion corrector 150 running on the computer 102.

Figure 2:
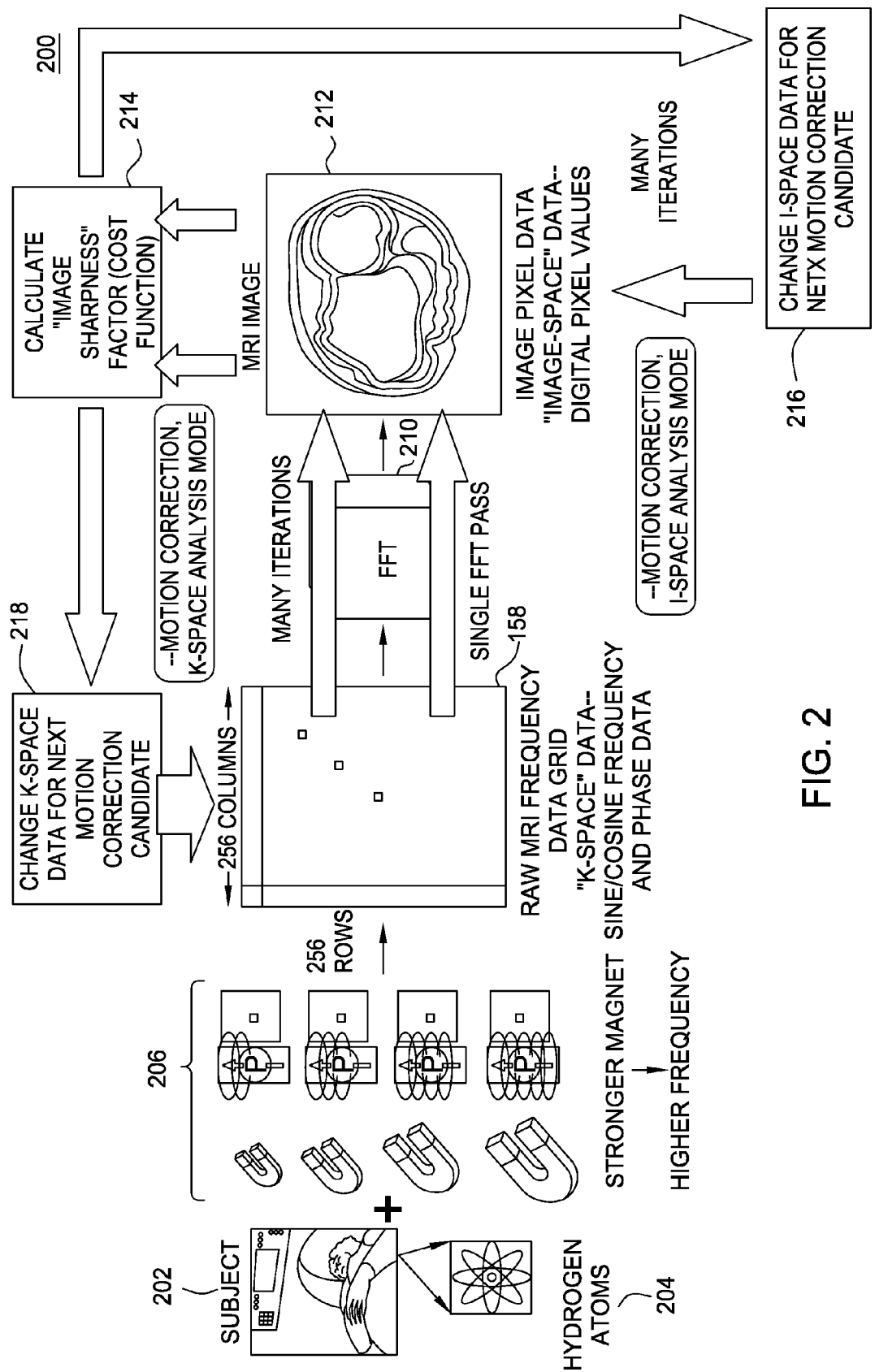
FIG. 2 is a data flow diagram illustrating motion correction in an MRI environment, according to one embodiment of the invention.

FIG. 2 is a data flow diagram 200 illustrating motion correction in an MRI environment, according to one embodiment of the invention. As shown, the data flow diagram 200 includes a subject 202, hydrogen atoms 204, and magnets 206. Further, the data flow diagram 200 includes k-space data 158, fast Fourier transform operations 210, graphical image 212 (also referred to herein as image space data, i-space data, and MRI image), operations 214 to evaluate the graphical image 212, operations 216 to consider a next candidate offset, and operations 218 to consider a next candidate motion.

Magnetic resonance imaging, or MRI, exploits magnetic properties of a hydrogen atom 204 to generate an image of the interior of a subject 202 (such as of a human body). MRI is a medical diagnostic technique that involves exposing a subject 202, such as a person, to a magnetic field of known strength (e.g., from a magnet 206). Hydrogen atoms 204 in the subject 202 have a resonant frequency proportional to the magnetic field 206. Because different parts of a subject (such as tissues of a human body) may have different hydrogen atom densities, hydrogen atom densities at different positions inside the subject may be measured to generate a graphical image 212.

In one embodiment, MRI image data may be acquired in the form of frequency data 152, or a frequency domain representation of the graphical image 212. For example, the frequency data 152 may include a 256×256 matrix of complex numbers. Each complex number may describe an amplitude and a phase of a component sinusoid, for a total of 65,536 (i.e., 256 times 256) component sinusoids. Further, each complex number/component sinusoid is sufficient to construct a sub-image of the subject (e.g., via the fast Fourier transform operations 210). The sub-images constructed from all of the complex numbers may be superimposed to generate the graphical image 212.

The motion corrector 150 may generate graphical images corresponding to rows of the k-space data 158 acquired at different points in time of the MRI scan, according to one embodiment. The motion corrector 150 may also determine an offset by which to superimpose the graphical images over each other to improve sharpness of a resulting image. The offset corresponds to, and compensates for, a movement of the subject during an MRI scan. The motion corrector 150 may also perform operations 216 to consider a next candidate offset.

In one embodiment, the motion corrector 150 may modify the k-space data (e.g., via the Fourier shift theorem) based on a determined offset, to compensate for subject motion to a finer resolution (i.e., finer than a discrete pixel resolution). In addition, the motion corrector 150 may perform operations 214 to evaluate a generated image 212 (i.e., from modified k-space data). The motion corrector 150 may also perform operations 218 to consider a next candidate motion (also based on the determined offset). The operations of the motion corrector 150 are further described below in conjunction with FIGS. 3 through 10.

Figure 3:
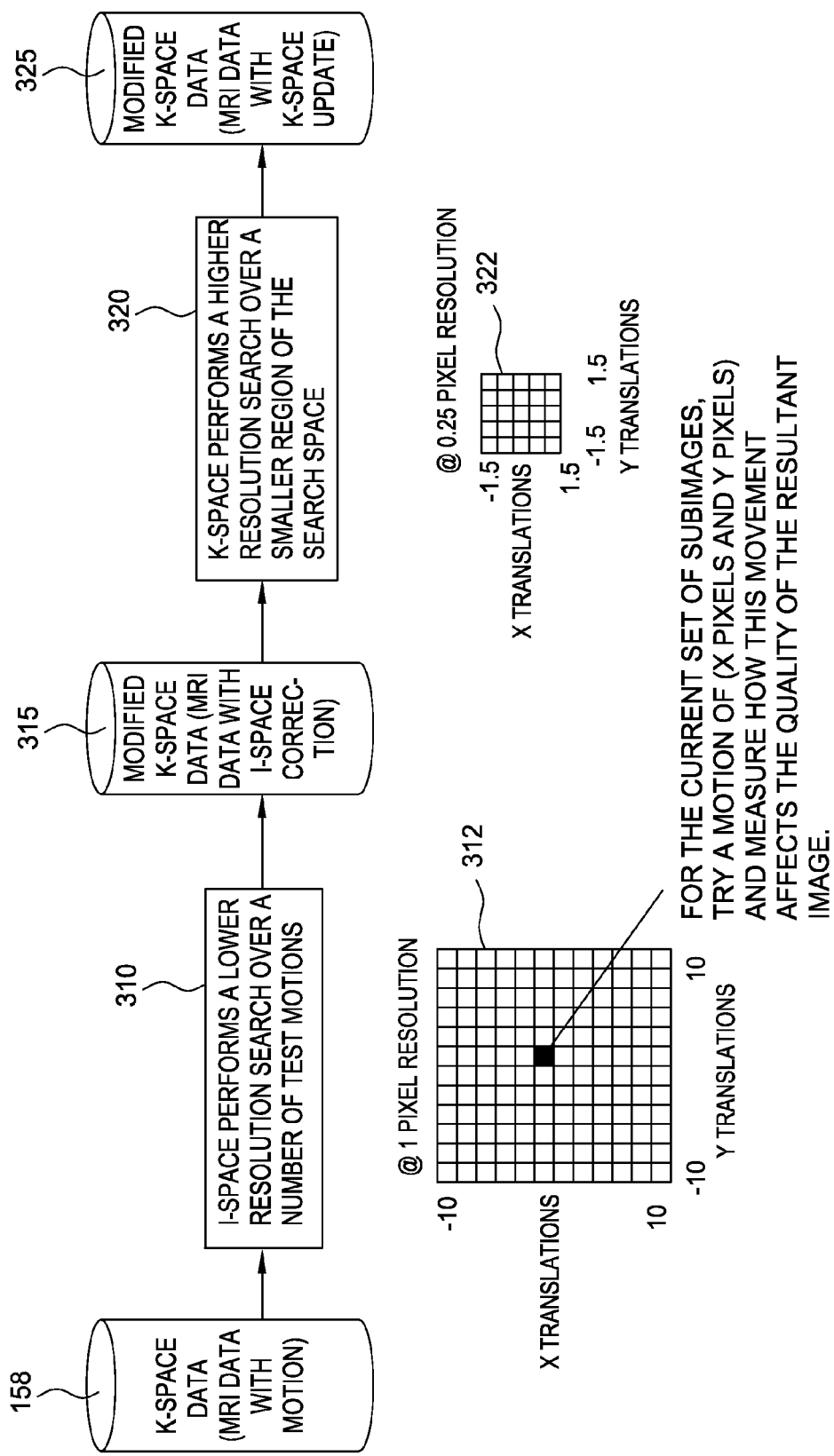
FIG. 3 is a flowchart depicting a method for compensating for motion of a subject during an MRI scan of the subject, according to one embodiment of the invention.

FIG. 3 is a flowchart depicting a method 300 for compensating for motion of a subject during an MRI scan of the subject, according to one embodiment of the invention. The method 300 may be performed by the motion corrector 150 of FIG. 1. As shown, the method 300 begins at step 310, where the motion corrector 150 receives k-space data 158 from an MRI scan of a subject. A first set of data elements of the k-space data 158 may be acquired at a different time than a second set of data elements of the k-space data 158. For example, at least one row of the k-space data 158 is acquired at a different time than another row of the k-space data 158. Other embodiments are broadly contemplated. For example, the first set of data may be a spiral pattern instead of a row pattern (or any other pattern). Further, the subject moves between a point in time that the first row of k-space data 158 is acquired and a second point in time at which the second row the k-space data 158 is acquired. As described in greater detail below, the motion corrector 150 compensates for such movement of the subject.

At step 310, the motion corrector 150 performs a first search of possible movements by the subject between the first point in time and the second point in time during the MRI scan. In one embodiment, the motion corrector 150 generates a first graphical image from the at least one row of the k-space data 158 acquired at the first point in time. Similarly, the motion corrector 150 generates a second graphical image from the at least one other row of the k-space data 158 acquired at the second point in time. The motion corrector 150 may then limit the first search to movements corresponding to an offset in pixels by which the second graphical image is superimposed onto the first graphical image (such as shown by a search grid 312). For example, for a 256×256 graphical image, the motion corrector 150 may restrict the search to a 21×21 grid at a 1-pixel resolution. The 21×21 grid may be centered on the 256×256 graphical image and includes offsets that may be measured on a vertical scale of minus ten pixels to plus ten pixels and on a horizontal scale of minus ten pixels to plus ten pixels, for a total of (21×21−1)=440 candidate offsets. Each candidate offset compensates for a patient movement (i.e., in the reverse direction). For example, an offset of (+4, +2) compensates for a patient movement of (−4, −2).

The first search may be described as "lower-resolution" relative to the search space of all possible movements by the subject between the first point in time and the second point in time. Further, the first search may be described as an image-space, or i-space, search. To evaluate each candidate movement, the motion corrector 150 may use the Fourier shift theorem to modify the at least one other row of k-space data to compensate for the candidate movement and to produce modified k-space data 325. The motion corrector 150 may then generate (e.g., via a discrete Fourier transform) a graphical image from the modified k-space data 320. The motion corrector 150 may evaluate a sharpness of the generated image (e.g., according to a cost function). For example, the cost function may compute, from a generated image, a value representing sharpness of the generated image. In one embodiment, the motion corrector determines, among the candidate offsets, an offset that yields the sharpest generated image.

At step 320, the motion corrector 150 performs a second search of possible movements by the subject between the first point in time and the second point in time during the MRI scan. The second search seeks to refine the results of the first search, according to one embodiment. The motion corrector 150 may determine candidate motions to search, based on the determined offset from the step 310. In contrast to the first search performed in the image space domain (e.g., by superimposing two graphical images at various offsets), the second search may operate directly on the modified k-space data 315 and may be described as a k-space search. During the second search, the motion corrector 150 may compensate for a candidate movement by modifying the k-space data using the Fourier shift theorem. In one embodiment, because the motion corrector 150 modifies a phase of a component sinusoid in the frequency domain representation of a graphical image (to compensate for translational movement of a subject), the motion corrector 150 may compensate for translational movement (of the subject) represented by any real number (as opposed to discrete pixels). That is, unlike the i-space search, the k-space search need not be limited to a discrete pixel resolution. The k-space search may be conducted over any real number (representing subject movement) that may be represented by the k-space data, according to one embodiment. However, the k-space search may be more computationally expensive than the i-space search. For example, the k-space search may require a 2D FFT for each point of the search space. In contrast, an i-space search may require only two 2D FFTs for the search space (specifically, to produce two sub-images to be translated by discrete pixel offsets over each other).

Because such a k-space search may be computationally expensive or even infeasible, the motion corrector 150 may restrict the k-space search based on the determined offset from the step 310, according to one embodiment. For example, the motion corrector 150 may restrict the k-space search to a 3×3 grid at a sub-pixel resolution. For instance, the motion corrector 150 may search a 3×3 grid at a sub-pixel resolution of 0.25 pixels, for a total distance of −1.5 to 1.5 pixels vertically and horizontally from the determined offset of the step 310 and for a total of (12×12−1)=143 candidate offsets (each compensating for a corresponding patient movement in the reverse direction). The 3×3 grid may include only movements that correspond to superimposing the second graphical image onto the first graphical image using the determined offset from the step 310 and further using a sub-pixel offset from the 3×3 grid (such as shown by a search grid 322).

In one embodiment, "sub-pixel" refers not to a magnitude of the offset but to a measuring unit of the offset. For example, "sub-pixel offset" need not entail that the k-space search is limited to offsets less than one pixel in the vertical or in the horizontal direction. For instance, four units of the 0.25-pixel offset yields a total offset of 1 pixel, and five units of the 0.25-pixel offset yields a total offset of 1.25 pixels. The motion corrector 150 may include, in the k-space search, any offset (even offsets exceeding one pixel) that is measured in a unit finer than a pixel. In effect, at the step 320, the motion corrector 150 performs a higher-resolution search (relative to the first search of the step 310) over a smaller area of the search space of the step 310.

Further, unlike the search in discrete pixel resolution (i.e., the i-space search performed at step 310), which the motion corrector 150 may perform using two graphical images (i.e., by superimposing one over the other at discrete pixel offsets), the sub-pixel search may include generating a graphical image for each sub-pixel offset to be evaluated. In other words, unlike discrete pixel offsets, which are applied in i-space, the sub-pixel offsets are applied in k-space (from which images are then generated), according to one embodiment.

Also at step 320, the motion corrector 150 may further modify the k-space data 315 to produce modified k-space data 325. The first search (at a discrete pixel resolution) and the second search (at a sub-pixel resolution) constitute searching in multiple resolutions, according to one embodiment. The motion corrector 150 may also combine the steps 310 and 320, according to one embodiment. For example, the motion corrector 150 may compute an overall offset based on the determined offset and the sub-pixel offset. For example, the motion corrector 150 may compute, from a determined offset of (−3,+5) and (+0.25,+0.25), an overall offset of (−2.75,+5.25). The motion corrector 150 may then modify the k-space data 158 based on the overall offset to produce the modified k-space data 325. After step 320 (or the combined steps 310 and 320), the method 300 terminates.

Figure 4A:
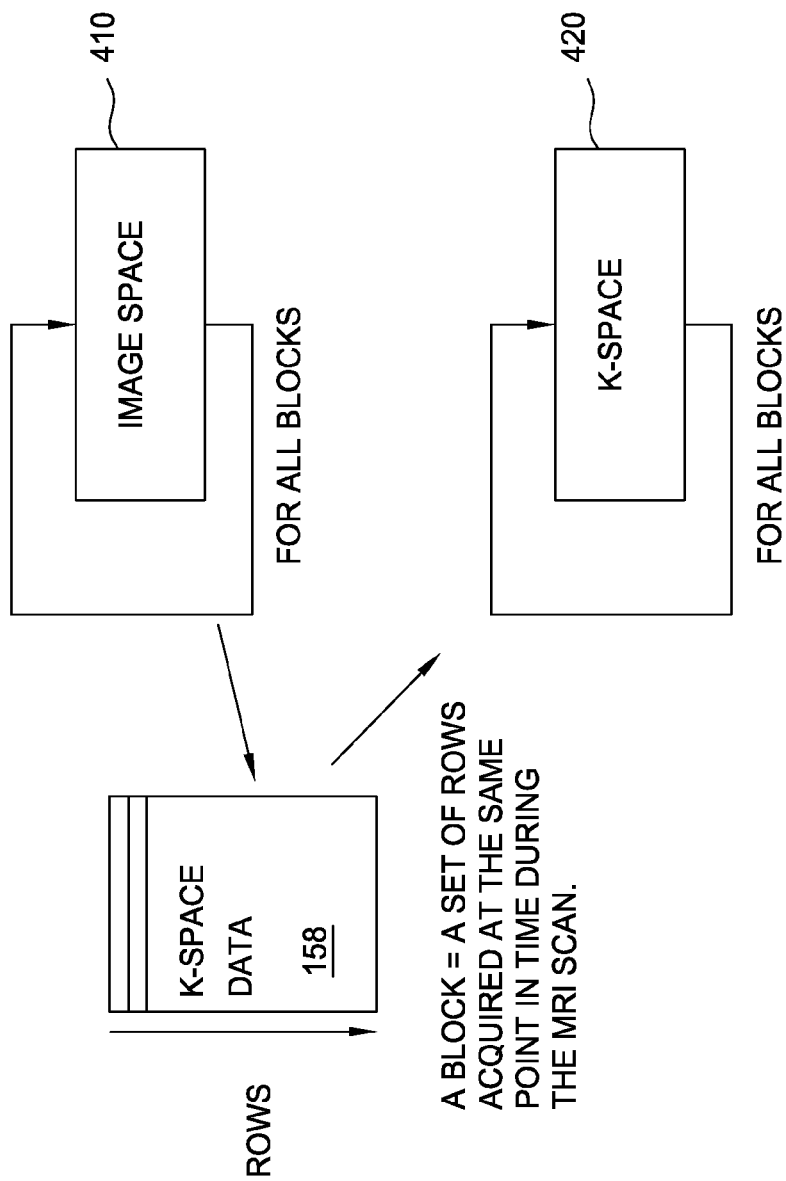
FIGS. 4A-4B illustrate methods for compensating for motion of a subject during an MRI scan of the subject, according to one embodiment of the invention.
Figure 4B:
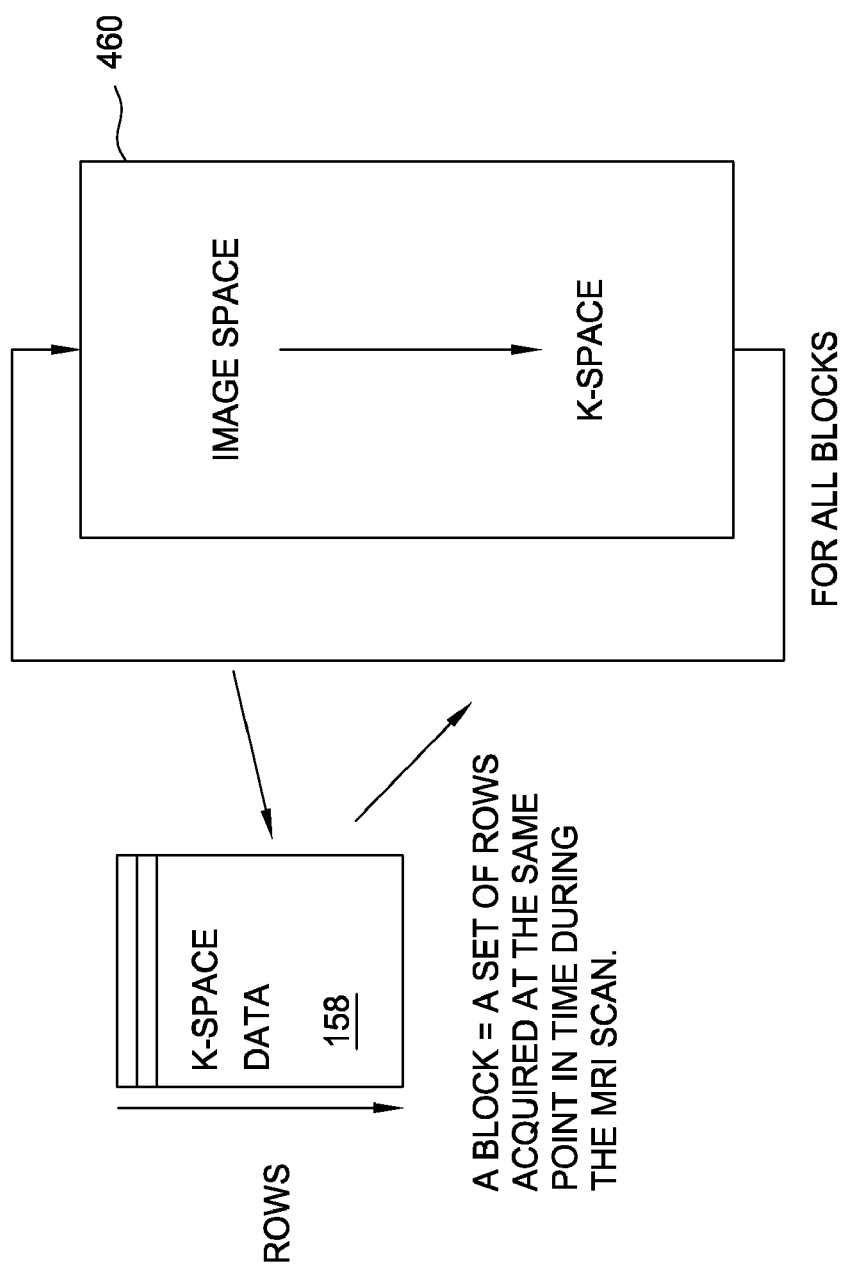

FIGS. 4A-4B illustrate methods 400, 450 for compensating for motion of a subject during an MRI scan of the subject, according to one embodiment of the invention. The methods 400, 450 may be performed by the motion corrector 150 of FIG. 1. As shown in FIG. 4A, the method 400 begins at step 410, where the motion corrector 150 compensates for motion for at least one block of the k-space data 158, at a pixel resolution. A block refers to a set of data elements (e.g., rows) acquired at the same point in time during the MRI scan of the subject. For example, suppose the k-space data 158 includes a first block acquired at a first point in time, a second block acquired at a second point in time, and a third block acquired at a third point in time. The motion corrector 150 may modify the second block and the third block to compensate for a discrete pixel (or coarser) motion of the patient between the first point in time and the second point in time. The motion corrector 150 may further modify the third block to compensate for a discrete pixel motion of the patient between the second point in time and the third point in time. In this manner, the motion corrector 150 at step 410 may compensate for discrete pixel motion for all blocks of the k-space data 158.

At step 420, the motion corrector 150 compensates for motion for at least one block of the k-space data 158, at a sub-pixel resolution. For example, the motion corrector 150 may modify the second block and the third block to compensate for a sub-pixel motion of the patient between the first point in time and the second point in time. The motion corrector 150 may further modify the third block to compensate for a sub-pixel motion of the patient between the second point in time and the third point in time. In this manner, the motion corrector 150 at step 420 compensates for sub-pixel motion for all blocks of the k-space data 158. After step 420, the method 400 terminates.

In one embodiment, the motion corrector 150 may combine the steps 410 and 420 of FIG. 4A. An example of this is shown in FIG. 4B. For example, as shown in FIG. 4B method 450 begins at step 460, where the motion corrector 150 compensates for discrete pixel (or coarser) motion for at least one block of the k-space data 158. Also at step 460, the motion corrector 150 compensates for sub-pixel motion for the at least one block of the k-space data 158. The motion corrector 150 may then repeat the step 460 for another at least one block of the k-space data. For example, the motion corrector 150 may modify the second block and the third block to compensate for a motion of the patient (at both discrete-pixel and sub-pixel resolutions) between the first point in time and the second point in time. The motion corrector 150 may then modify the third block to compensate for a motion of the patient (at both discrete-pixel and sub-pixel resolutions) between the second point in time and the third point in time. When no blocks remain to be processed, the method 450 terminates.

Figure 5:
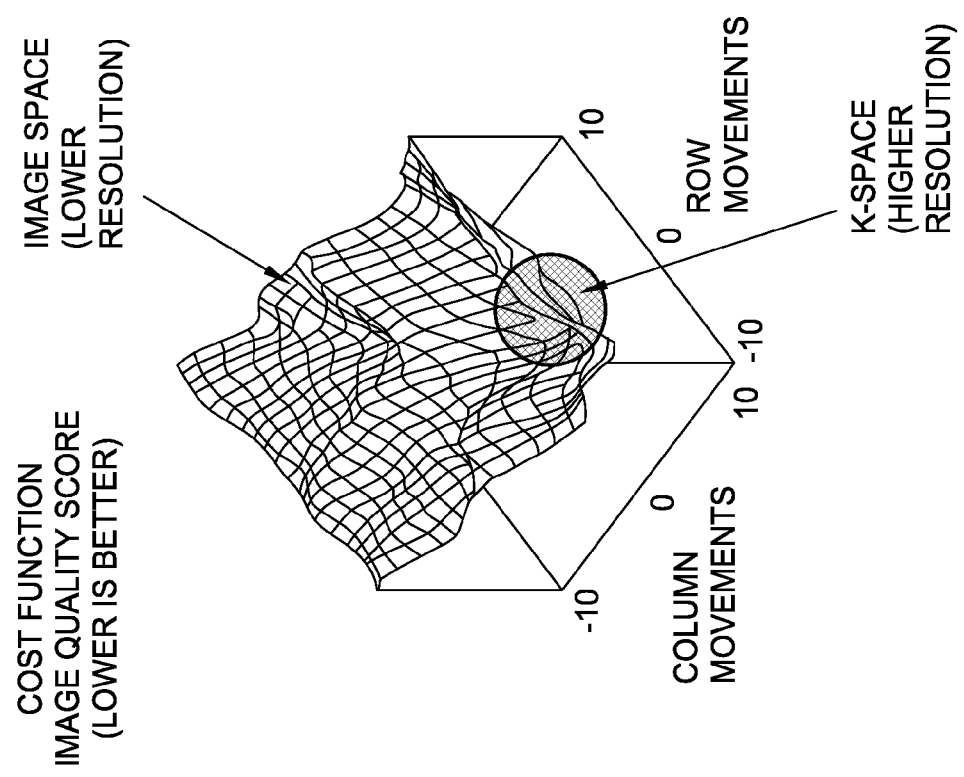
FIG. 5 illustrates a cost function for candidate subject movements within an i-space search at a discrete pixel resolution, according to one embodiment of the invention.

FIG. 5 illustrates a cost function 500 for candidate subject movements within the i-space search at a discrete pixel resolution (i.e., the 21×21 grid) of FIG. 3, according to one embodiment of the invention. The motion corrector 150 may perform the i-space search at a discrete pixel resolution within the 21×21 grid to identify an offset that yields the sharpest graphical image, according to one embodiment. As shown, the cost function 500 evaluates a graphical image generated from each candidate offset to compute a score representing sharpness of the respective graphical image (a lower sharpness score is better than a higher sharpness score in this example). The motion corrector 150 may identify the discrete pixel offset that yields the sharpest graphical image. The motion corrector 150 may then perform a k-space search at a sub-pixel resolution within a smaller area (e.g., a 3×3 grid, or the area 502), relative to the identified offset. For example, the motion corrector 150 may include a cost function 500 that evaluates a graphical image generated from each sub-pixel offset (i.e., relative to the identified offset) to compute a score representing sharpness of the respective graphical image. The motion corrector 150 may identify the sub-pixel offset (relative to the identified offset) that yields the sharpest graphical image.

Figure 6:
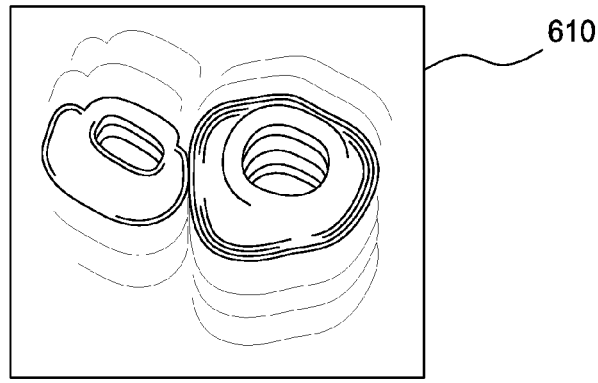
FIG. 6 illustrates graphical images generated from an MRI scan of two human fingers, according to one embodiment of the invention.
Figure 6:
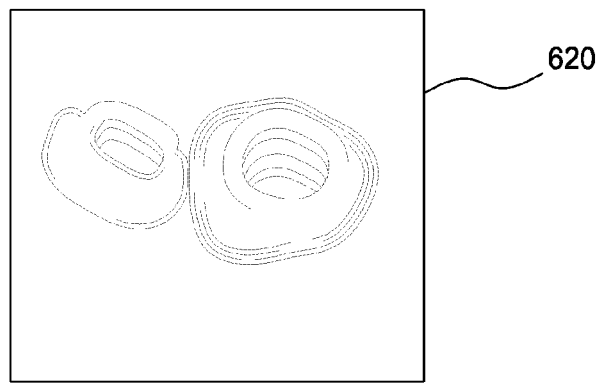
Figure 6:
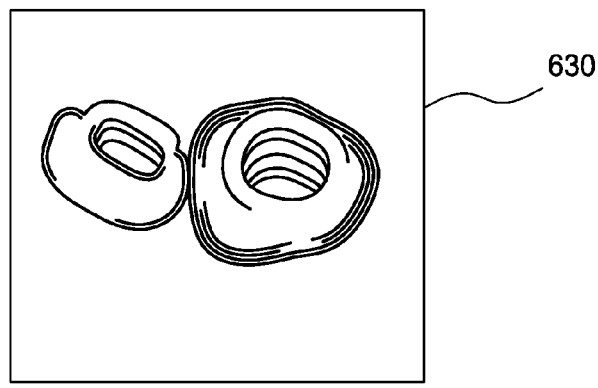

FIG. 6 illustrates an example of graphical images 600 generated from an MRI scan of two human fingers, according to one embodiment of the invention. The graphical images 600 may be generated by the motion corrector 150 of FIG. 1. As shown, the graphical images 600 include a first graphical image 610 generated from the k-space data. The blur of the first graphical image 610 is due to the subject moving during the MRI scan. The graphical images 600 also include a second graphical image 620 generated from an i-space search (i.e., at a discrete pixel resolution). As shown, the second graphical image 620 is sharper than the first graphical image 610. The increase in sharpness in the second graphical image 620 results from i-space motion correction of the first graphical image 610. The graphical images 600 also include a third graphical image 630 generated from an i-space search (i.e., at a discrete pixel resolution) followed by a k-space search (i.e., at a sub-pixel resolution). As shown, the third graphical image 630 is sharper than both the first graphical image 610 and the second graphical image 620. The increase in sharpness in the third graphical image 630 is achieved by performing a k-space search at a sub-pixel resolution within a limited area relative to an offset identified from performing an i-space search, according to one embodiment. While at the same time, the techniques of the present invention allow searches for motion correction to be performed in a reasonable time.

Figure 7:
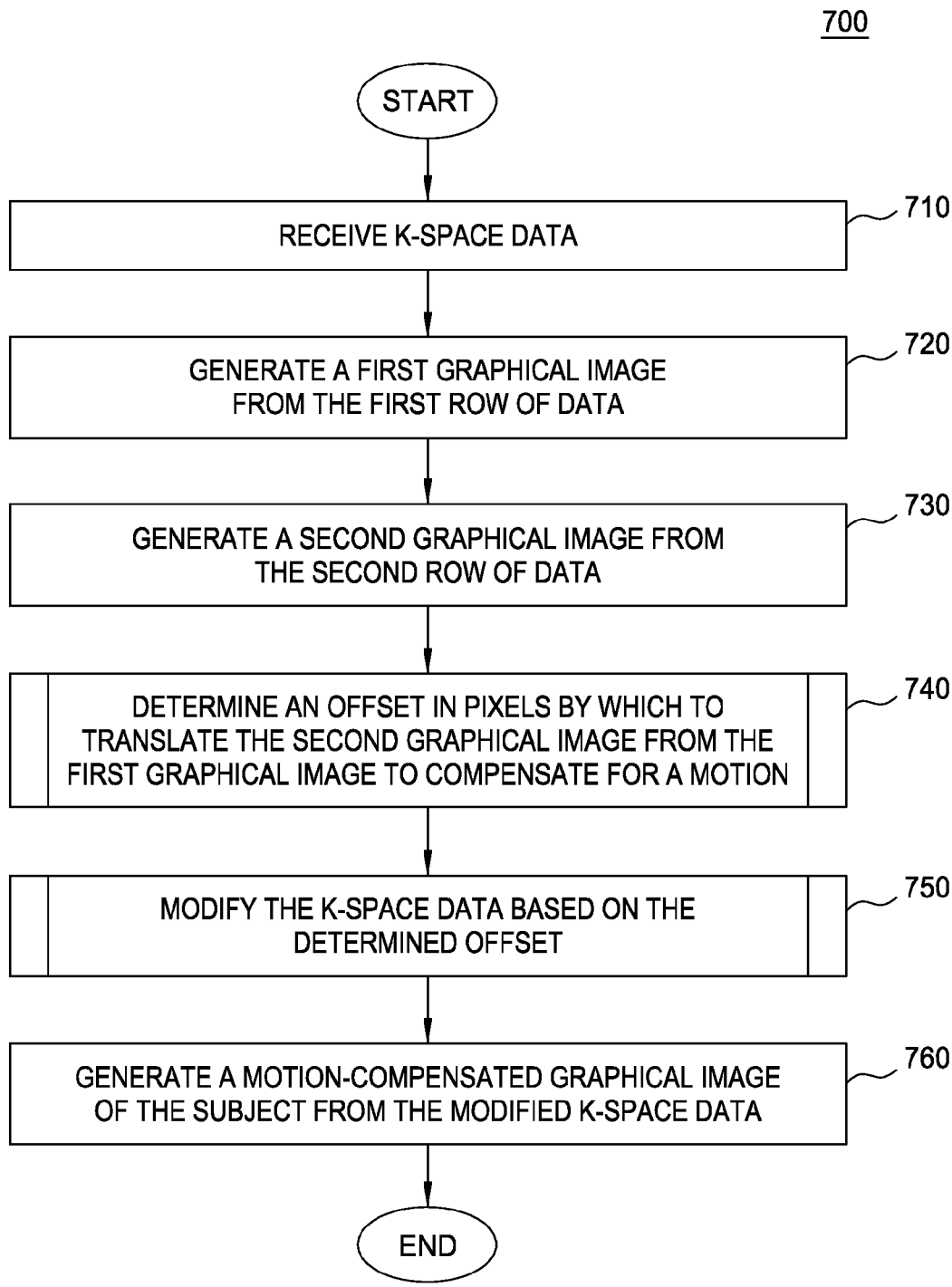
FIG. 7 is a flowchart depicting a method for compensating for motion of a subject during an MRI scan of the subject, according to one embodiment of the invention.

FIG. 7 is a flowchart depicting a method 700 for compensating for motion of a subject during an MRI scan of the subject, according to one embodiment of the invention. The method 700 may be performed by the motion corrector 150 of FIG. 1 and corresponds to the steps 310 and 320 of FIG. 3. As shown, the method 700 begins at step 710, where the motion corrector 150 receives k-space data 158 acquired from the MRI scan. The k-space data is a frequency domain data acquired from the MRI scan and from which a graphical image of the subject may be generated. Further, the k-space data includes rows of data, according to one embodiment. At step 720, the motion corrector 150 generates a first graphical image 152 from a first row of data acquired at a first point in time during the MRI scan. The first row of data may not necessarily correspond to any "row" of pixels in the first graphical image generated from the first row of data. Because the entire first row of data is acquired at a single point in time during the MRI scan, the entire first row of data reflects only a single location of a subject being scanned. Thus, the entire first row of data may be treated as a single unit for purposes of motion correction. At step 730, the motion corrector 150 generates a second graphical image 154 from a second row of data acquired at a second point in time during the MRI scan.

At step 740, the motion corrector 150 determines an offset in pixels by which to translate the second graphical image from the first graphical image to compensate for subject movement. The step 740 is further described below in conjunction with FIG. 8. At step 750, the motion corrector 150 modifies the k-space data based on the offsets determined at the step 740. That is, the motion corrector 150 compensates for the motion to a sub-pixel offset relative to the determined offset. The step 750 is further described below in conjunction with FIG. 9. At step 760, the motion corrector 150 generates a motion-compensated graphical image 156 of the subject from the modified k-space data 158. An example of a motion-compensated graphical image 156 is the graphical image 630 of FIG. 6. After the step 760, the method 700 terminates.

Figure 8:
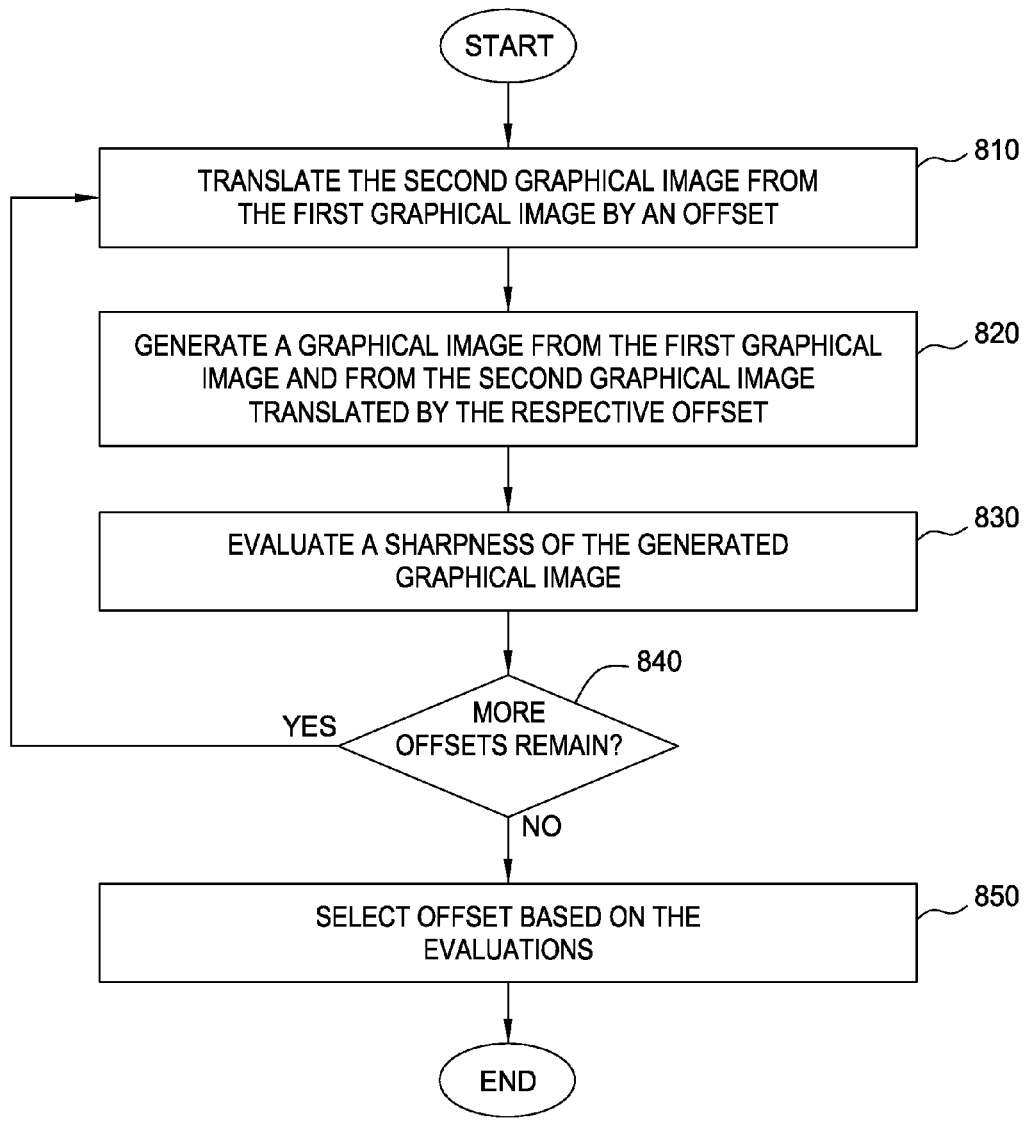
FIG. 8 is a flowchart depicting a method for compensating for motion of a subject in i-space, according to one embodiment of the invention.

FIG. 8 is a flowchart depicting a method 800 for compensating for motion of a subject in i-space (e.g., at a discrete pixel resolution), according to one embodiment of the invention. The method 800 may be performed by the motion corrector 150 of FIG. 1. Further, the method 800 may correspond to the step 740 of FIG. 7. As shown, the method 800 begins at step 810, where the motion corrector 150 translates the second graphical image from the first graphical image by an offset. At step 820, the motion corrector 150 generates a graphical image from (e.g., via superimposing) the first graphical image and from the second graphical image translated by the respective offset. For example, the first graphical image and the second graphical image (translated by the offset) may be superimposed as follows. Performing a 2D FFT of complex numbers (e.g., of the k-space data) produces another set of complex numbers (regarded as i-space data) from which a graphical image may be generated (e.g., by computing a magnitude of each complex number). The first graphical image and the second graphical image may be superimposed by performing complex addition of the i-space data of the two respective graphical images. The superimposed image may then be generated from the summed i-space complex data.

At step 830, the motion corrector 150 evaluates a sharpness of the generated graphical image. At step 840, the motion corrector 150 determines whether more offsets remain to be evaluated. If so, the method 800 returns to the step 810, where the motion corrector 150 evaluates a next offset. For example, the motion corrector 150 may evaluate every discrete pixel offset of the 21×21 grid of FIG. 3 (i.e., for a total of 440 candidate offsets). Otherwise, the motion corrector selects an offset based on the evaluations (step 850). For example, the motion corrector 150 may select, of the evaluated offsets, an offset that yields the sharpest graphical image. After the step 850, the method 800 terminates.

Figure 9:
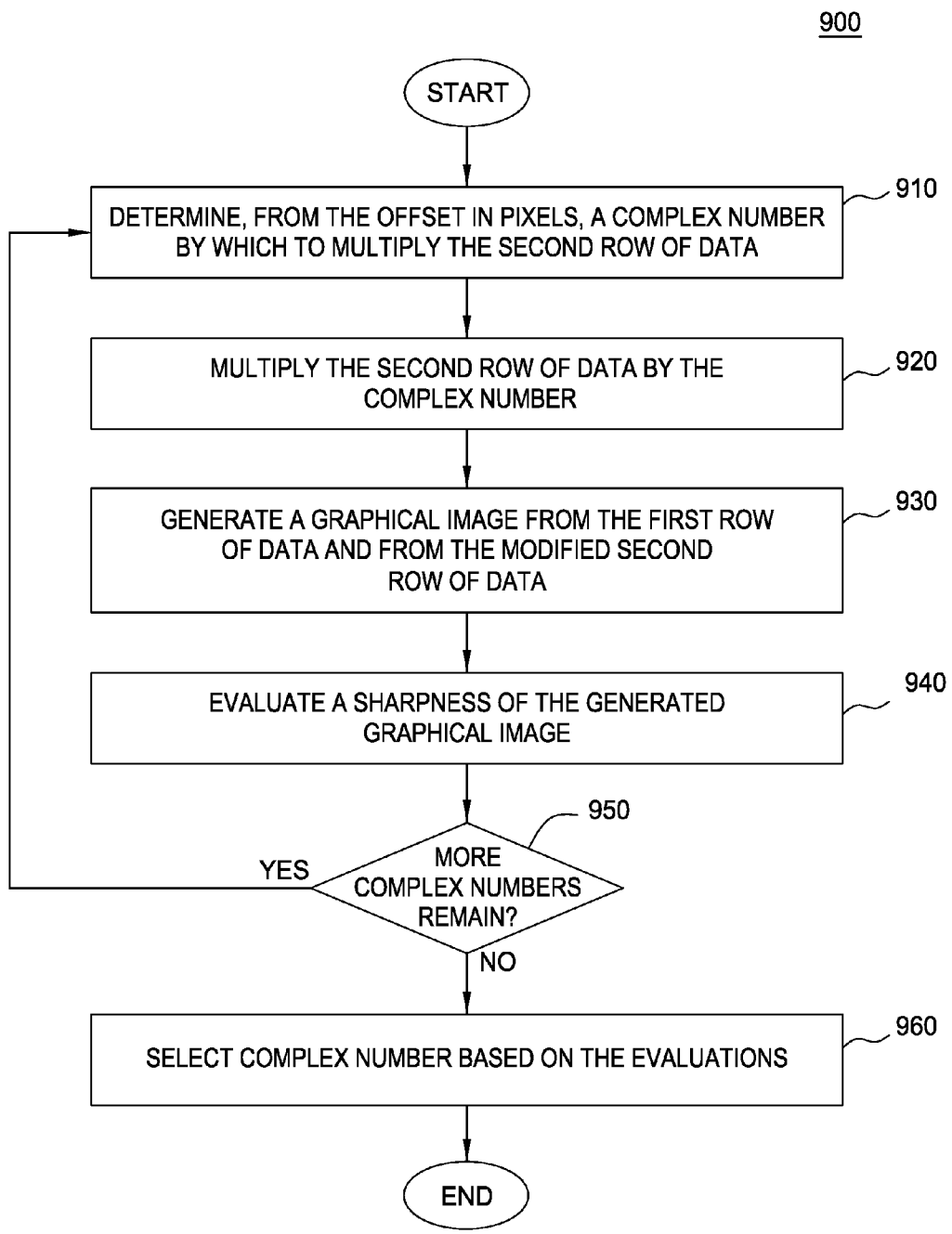
FIG. 9 is a flowchart depicting a method for compensating for motion of a subject in k-space, according to one embodiment of the invention.

FIG. 9 is a flowchart depicting a method 900 for compensating for motion of a subject in k-space (e.g., at a sub-pixel resolution), according to one embodiment of the invention. The method 900 may be performed by the motion corrector 150 of FIG. 1. Further, the method 900 may correspond to the step 750 of FIG. 7. As shown, the method 900 begins at step 910, where the motion corrector 150 determines, from the selected pixel offset (of the step 850 of FIG. 8), a complex number by which to multiply the second row of data. Multiplying the second row of data by the complex number compensates for motion by, in effect, translating a sub-image (corresponding to the second row of data) by the selected pixel offset and a sub-pixel offset from the selected pixel offset, according to one embodiment. A sub-image refers to a graphical image generated only from a set of data elements acquired at a single point in time during the MRI scan, according to one embodiment. The motion corrector 150 may determine the complex number by applying the Fourier shift theorem using the selected pixel offset and the sub-pixel offset.

At step 920, the motion corrector 150 multiplies the second row of data by the complex number. At step 930, the motion corrector 150 generates a graphical image from the first row of data and from the modified second row of data. At step 940, the motion corrector 150 evaluates a sharpness of the generated graphical image. At step 950, the motion corrector 150 determines whether more complex numbers (e.g., more sub-pixel offsets from the determined offset) remain to be evaluated. If so, the method 900 returns to the step 910, where the motion corrector 150 evaluates a next sub-pixel offset from the selected pixel offset. For example, the motion corrector 150 may evaluate the 3×3 grid of FIG. 3 at a 0.25-pixel resolution (i.e., for a total of 143 candidate sub-pixel offsets). Otherwise, the motion corrector 150 selects a complex number (e.g., a sub-pixel offset) based on the evaluations (step 960). For example, the motion corrector 150 may select, of the evaluated sub-pixel offsets from the selected offset, a sub-pixel offset that yields the sharpest graphical image. After the step 960, the method 900 terminates.

Figure 10:
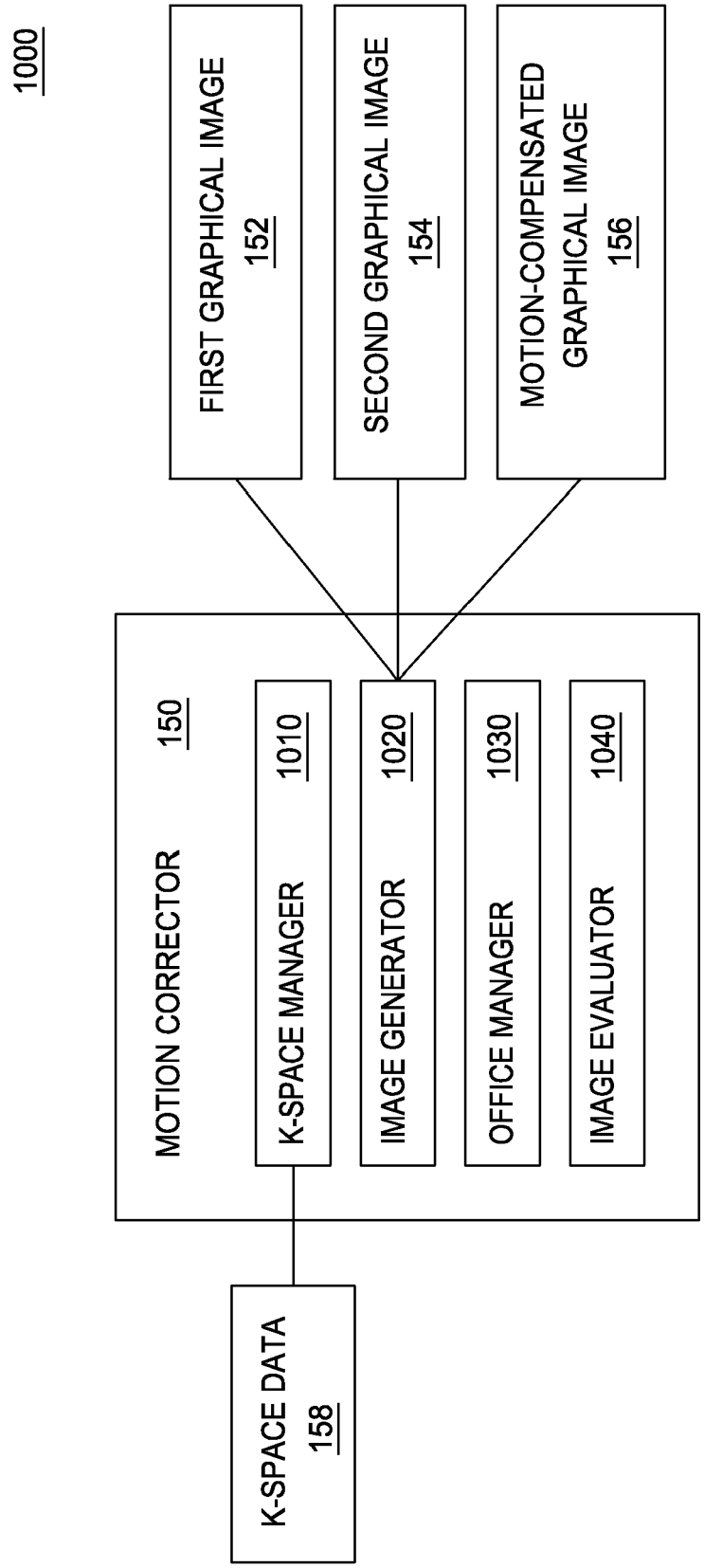
FIG. 10 is a block diagram illustrating components of a motion corrector, according to one embodiment of the invention.

FIG. 10 is a block diagram illustrating components 1000 of the motion corrector 150 of FIG. 1, according to one embodiment of the invention. As shown, the motion corrector 150 includes a k-space manager 1010, an image generator 1020, an offset manager 1030, and an image evaluator 1040.

In one embodiment, the k-space manager 1010 receives the k-space data 158 from an MRI scan of a subject. The image generator 1020 creates graphical images from the k-space data 158, according to one embodiment. For example, the image generator 1020 may create a first graphical image 152 and a second graphical image 154 for an i-space search. Further, the image generator 1020 may create a graphical image for each sub-pixel offset during a k-space search. The image generator 1020 may also create a motion-compensated graphical image 156 from the i-space search and the k-space search. The motion-compensated graphical image 156 may, for example, depict at least part of a human body. The motion corrector 150 may output the motion-compensated graphical image 156 to the output device 116, according to one embodiment.

In one embodiment, the offset manager 1030 determines candidate offsets to be evaluated during the i-space search. The offset manager 1030 may also determine candidate sub-pixel offsets to be evaluated during the k-space search. The image evaluator 1040 assesses graphical images generated during the i-space search and the k-space search (e.g., using a cost function for image sharpness). The motion corrector 150 may select a pixel offset and a sub-pixel offset based on the assessments, according to one embodiment.

Of course, the embodiments described herein are intended to be illustrative and not limiting of the invention, and other embodiments are broadly contemplated. Those skilled in the art will recognize, for example, that embodiments of the invention may be adapted to support other types of motion, data formats, and techniques for capturing motion information as well as other imaging technology where subject movements that occur during the image acquisition process may degrade image quality or clarity.

Advantageously, embodiments of the invention compensate for motion of a subject during an MRI scan of the subject. In one embodiment, a motion corrector may receive k-space data from the MRI scan of the subject. The k-space data may include a frequency domain representation of a graphical image of the subject. Further, the k-space data may include a first row of data acquired at a first point in time during the MRI scan and a second row of data acquired at a second point in time during the MRI scan. The motion corrector may generate a first graphical image from the first row of data. Similarly, the motion corrector may generate a second graphical image from the second row of data. The motion corrector may determine an offset in pixels by which to translate the second graphical image from the first graphical image to compensate for the motion. Further, the motion corrector may modify the k-space data based on the determined offset to compensate for the motion to a sub-pixel offset relative to the determined offset. The motion corrector may generate a motion-compensated graphical image of the subject from the modified k-space data.

While the foregoing is directed to embodiments of the present invention, other and further embodiments of the invention may be devised without departing from the basic scope thereof, and the scope thereof is determined by the claims that follow.

What is claimed is:

1. A computer-implemented method for compensating for motion of a subject during a magnetic resonance imaging (MRI) scan of the subject, comprising:
    receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan;
    generating a first graphical image from the first set of data elements;
    generating a second graphical image from the second set of data elements;
    determining an offset in pixels by which to translate the second graphical image from the first graphical image to compensate for the motion based on evaluating, for each offset of a plurality of distinct offsets, a sharpness of a graphical image generated from the first graphical image and the second graphical image translated by the respective offset;
    modifying the k-space data based on the determined offset to compensate for the motion to a sub-pixel offset, relative to the determined offset; and
    generating a motion-compensated graphical image of the subject from the modified k-space data.

2. The computer-implemented method of claim 1, wherein the motion-compensated graphical image of the subject depicts a part of a human body.

3. The computer-implemented method of claim 1, wherein modifying the k-space data based on the determined offset to compensate for the motion to a sub-pixel offset relative to the determined offset comprises:
    determining, from the offset in pixels, a plurality of sub-pixel offsets relative to the offset in pixels by which to translate the second graphical image from the first graphical image to compensate for the motion;
    for each of the determined sub-pixel offsets:
        determining a complex number from the offset in pixels and the respective sub-pixel offset,
        multiplying the second set of data elements by the respective determined complex number,
        generate a graphical image from the first set of data elements and from the modified second set of data elements, and
        evaluating a sharpness of the generated graphical image; and
    selecting the sub-pixel offset based on the respective sharpness of each generated graphical image.

4. The computer-implemented method of claim 3, wherein the second set of data elements is multiplied by the respective determined complex number to modify a phase of at least one sinusoid represented by the second set of data elements.

5. The computer-implemented method of claim 3, wherein the complex number is determined using the Fourier shift theorem.

6. The computer-implemented method of claim 1, wherein generating the motion-compensated graphical image of the subject comprises performing a two-dimensional discrete Fourier transform on the k-space data.

7. A computer readable storage medium containing a program which, when executed, performs an operation for compensating for motion of a subject during a magnetic resonance imaging (MRI) scan of the subject, the operation comprising:
    receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan;
    generating a first graphical image from the first set of data elements;
    generating a second graphical image from the second set of data elements;
    determining an offset in pixels by which to translate the second graphical image from the first graphical image to compensate for the motion based on evaluating, for each offset of a plurality of distinct offsets, a sharpness of a graphical image generated from the first graphical image and the second graphical image translated by the respective offset;

modifying the k-space data by operation of one or more computer processors when executing the program and based on the determined offset to compensate for the motion to a sub-pixel offset, relative to the determined offset; and generating a motion-compensated graphical image of the subject from the modified k-space data.

8. The computer readable storage medium of claim 7, wherein the motion-compensated graphical image of the subject depicts at least part of a human body.

9. The computer readable storage medium of claim 7, wherein modifying the k-space data based on the determined offset to compensate for the motion to a sub-pixel offset relative to the determined offset comprises:

determining, from the offset in pixels, a plurality of sub-pixel offsets relative to the offset in pixels by which to translate the second graphical image from the first graphical image to compensate for the motion;

for each of the determined sub-pixel offsets:
determining a complex number from the offset in pixels and the respective sub-pixel offset,
multiplying the second set of data elements by the respective determined complex number,
generate a graphical image from the first set of data elements and from the modified second set of data elements, and
evaluating a sharpness of the generated graphical image; and selecting the sub-pixel offset based on the respective sharpness of each generated graphical image.

10. The computer readable storage medium of claim 9, wherein the second set of data elements is multiplied by the respective determined complex number to modify a phase of at least one sinusoid represented by the second set of data elements.

11. The computer readable storage medium of claim 9, wherein the complex number is determined using the Fourier shift theorem.

12. The computer readable storage medium of claim 7, wherein generating the motion-compensated graphical image of the subject comprises performing a two-dimensional discrete Fourier transform on the k-space data.

13. A system, comprising:
one or more computer processors; and
a memory containing a program, which when executed by the one or more computer processors is configured to perform an operation for compensating for motion of a subject during a magnetic resonance imaging (MRI) scan of the subject, the operation comprising:
receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan,
generating a first graphical image from the first set of data elements;
generating a second graphical image from the second set of data elements,
determining an offset in pixels by which to translate the second graphical image from the first graphical image to compensate for the motion based on evaluating, for each offset of a plurality of distinct offsets, a sharpness of a graphical image generated from the first graphical image and the second graphical image translated by the respective offset,
modifying the k-space data based on the determined offset to compensate for the motion to a sub-pixel offset, relative to the determined offset, and
generating a motion-compensated graphical image of the subject from the modified k-space data.

14. The system of claim 13, wherein the motion-compensated graphical image of the subject depicts at least part of a human body.

15. The system of claim 13, wherein modifying the k-space data based on the determined offset to compensate for the motion to a sub-pixel offset relative to the determined offset comprises:

determining, from the offset in pixels, a plurality of sub-pixel offsets relative to the offset in pixels by which to translate the second graphical image from the first graphical image to compensate for the motion;

for each of the determined sub-pixel offsets:
determining a complex number from the offset in pixels and the respective sub-pixel offset,
multiplying the second set of data elements by the respective determined complex number,
generate a graphical image from the first set of data elements and from the modified second set of data elements, and
evaluating a sharpness of the generated graphical image; and selecting the sub-pixel offset based on the respective sharpness of each generated graphical image.

16. The system of claim 15, wherein the second set of data elements is multiplied by the respective determined complex number to modify a phase of at least one sinusoid represented by the second set of data elements.

17. The system of claim 15, wherein the complex number is determined using the Fourier shift theorem.

18. The system of claim 13, wherein generating the motion-compensated graphical image of the subject comprises performing a two-dimensional discrete Fourier transform on the k-space data.

19. A computer-implemented method for compensating for motion of a subject during a magnetic resonance imaging (MRI) scan of the subject, comprising:
receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan;
generating a first graphical image from the first set of data elements;
generating a second graphical image from the second set of data elements;
determining an offset in pixels by which to translate the second graphical image from the first graphical image to compensate for the motion;
modifying the k-space data based on the determined offset to compensate for the motion to a sub-pixel offset, relative to the determined offset, wherein the sub-pixel offset is selected based on evaluating, for each sub-pixel offset of a plurality of distinct sub-pixel offsets, a sharpness of a graphical image generated from the first set of data elements and from the second set of data elements multiplied by a complex number determined from the offset in pixels and the respective sub-pixel offset; and generating a motion-compensated graphical image of the subject from the modified k-space data.

20. A computer readable storage medium containing a program which, when executed, performs an operation for compensating for motion of a subject during a magnetic resonance imaging (MRI) scan of the subject, the operation comprising:

receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan;

generating a first graphical image from the first set of data elements;

generating a second graphical image from the second set of data elements;

determining an offset in pixels by which to translate the second graphical image from the first graphical image to compensate for the motion;

modifying the k-space data by operation of one or more computer processors when executing the program and based on the determined offset to compensate for the motion to a sub-pixel offset, relative to the determined offset, wherein the sub-pixel offset is selected based on evaluating, for each sub-pixel offset of a plurality of distinct sub-pixel offsets, a sharpness of a graphical image generated from the first set of data elements and from the second set of data elements multiplied by a complex number determined from the offset in pixels and the respective sub-pixel offset; and generating a motion-compensated graphical image of the subject from the modified k-space data.

21. A system, comprising:

one or more computer processors; and a memory containing a program, which when executed by the one or more computer processors is configured to perform an operation for compensating for motion of a subject during a magnetic resonance imaging (MRI) scan of the subject, the operation comprising:

receiving k-space data from the MRI scan of the subject, wherein the k-space data comprises frequency domain data acquired from the MRI scan used to generate a graphical image of the subject, wherein the frequency domain representation includes a plurality of data elements, and wherein the plurality of data elements includes a first set of data elements acquired at a first point in time during the MRI scan and a second set of data elements acquired at a second point in time during the MRI scan, generating a first graphical image from the first set of data elements, generating a second graphical image from the second set of data elements, determining an offset in pixels by which to translate the second graphical image from the first graphical image to compensate for the motion, modifying the k-space data based on the determined offset to compensate for the motion to a sub-pixel offset, relative to the determined offset, wherein the sub-pixel offset is selected based on evaluating, for each sub-pixel offset of a plurality of distinct sub-pixel offsets, a sharpness of a graphical image generated from the first set of data elements and from the second set of data elements multiplied by a complex number determined from the offset in pixels and the respective sub-pixel offset, and generating a motion-compensated graphical image of the subject from the modified k-space data.

* * * * *